US00PP24871P3

(12) United States Plant Patent
Olesen

(10) Patent No.: US PP24,871 P3
(45) Date of Patent: Sep. 16, 2014

(54) ROSE PLANT NAMED 'POULCOT012'

(50) Latin Name: ***Rosa* hybrid**
Varietal Denomination: Poulcot012

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 166 days.

(21) Appl. No.: 13/507,040

(22) Filed: May 31, 2012

(65) Prior Publication Data

US 2013/0326739 P1 Dec. 5, 2013

(51) Int. Cl.
*A01H 5/00* (2006.01)

(52) U.S. Cl.
USPC ..... Plt./108

(58) Field of Classification Search
CPC ..... A01H 5/022
USPC ..... Plt./108
See application file for complete search history.

(56) References Cited

PUBLICATIONS

UPOV PLUTO Citation for Poulcot012 Apr. 2, 2013.*

* cited by examiner

*Primary Examiner* — Wendy C Haas

(57) ABSTRACT

A new garden rose plant of the Shrub class which has abundant, red flowers and attractive foliage. This new and distinct variety has shown to be uniform and stable in the resulting generations from asexual propagation.

3 Drawing Sheets

Botanical designation: *Rosa* hybrid.
Variety denomination: 'Poulcot012'.

SUMMARY OF THE INVENTION

The present invention constitutes a new and distinct variety of garden rose plant which originated from a controlled crossing between the female seed parent, an unnamed unpatented seedling, and the male pollen parent, also an unnamed unpatented seedling.

The two parents were crossed during the summer of 2003 and the resulting seeds were planted in a controlled environment in Fredensborg, Denmark. The new variety, named 'Poulcot012', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance; and
4. Abundant rose hips.

This combination of qualities is not present in previously available commercial cultivars of this type, known to the inventor, and distinguish 'Poulcot012' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcot012' was selected in the spring of 2004 by the inventor as a single plant from the progeny of the aforementioned hybridization.

Asexual reproduction of 'Poulcot012' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcot012' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcot012'. Specifically illustrated in the drawing are flowers at various stages of development, flower in parts, leaves, and stems.

DETAILED DESCRIPTION OF THE VARIETY

Figure 1:
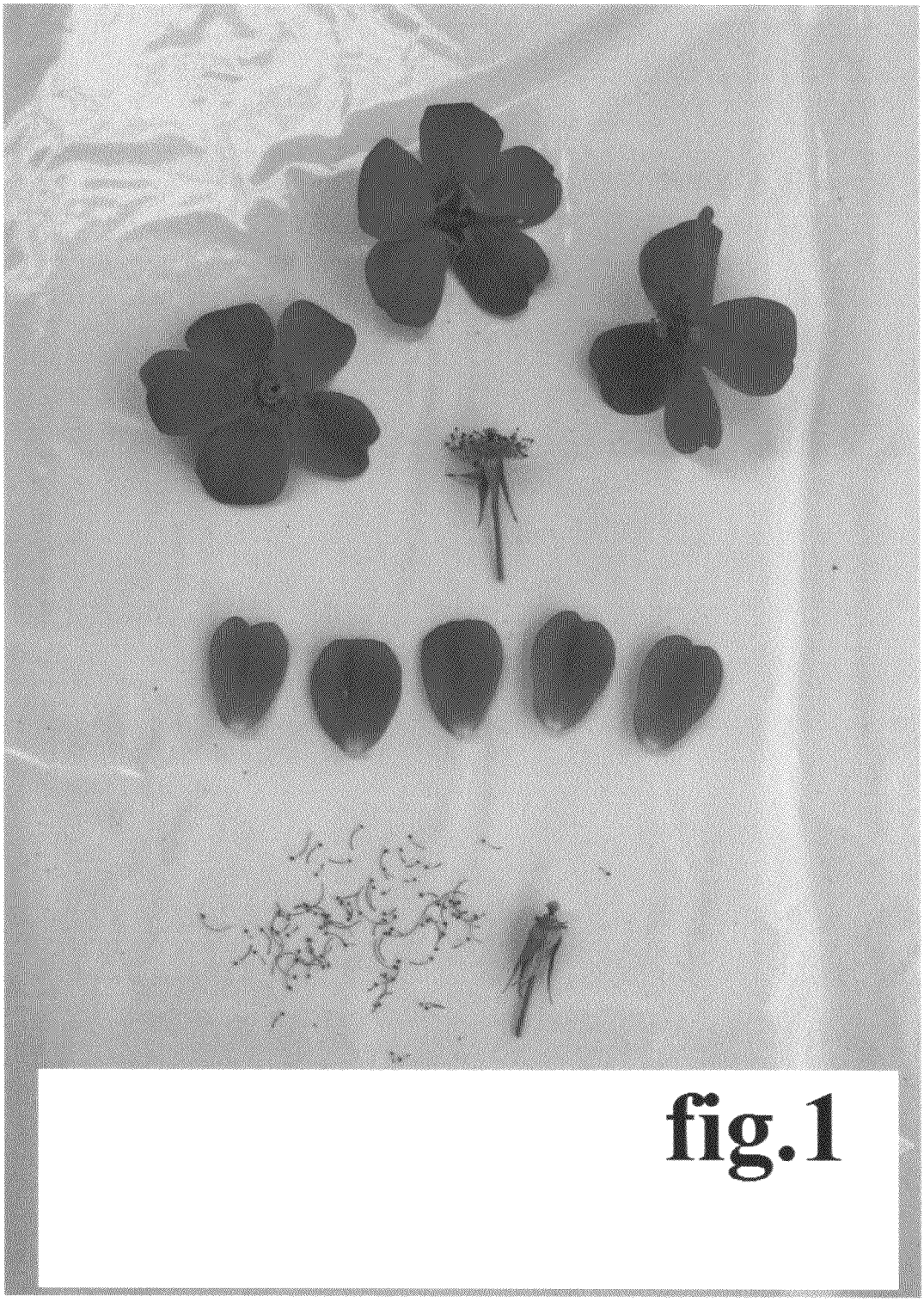
Figure 2:
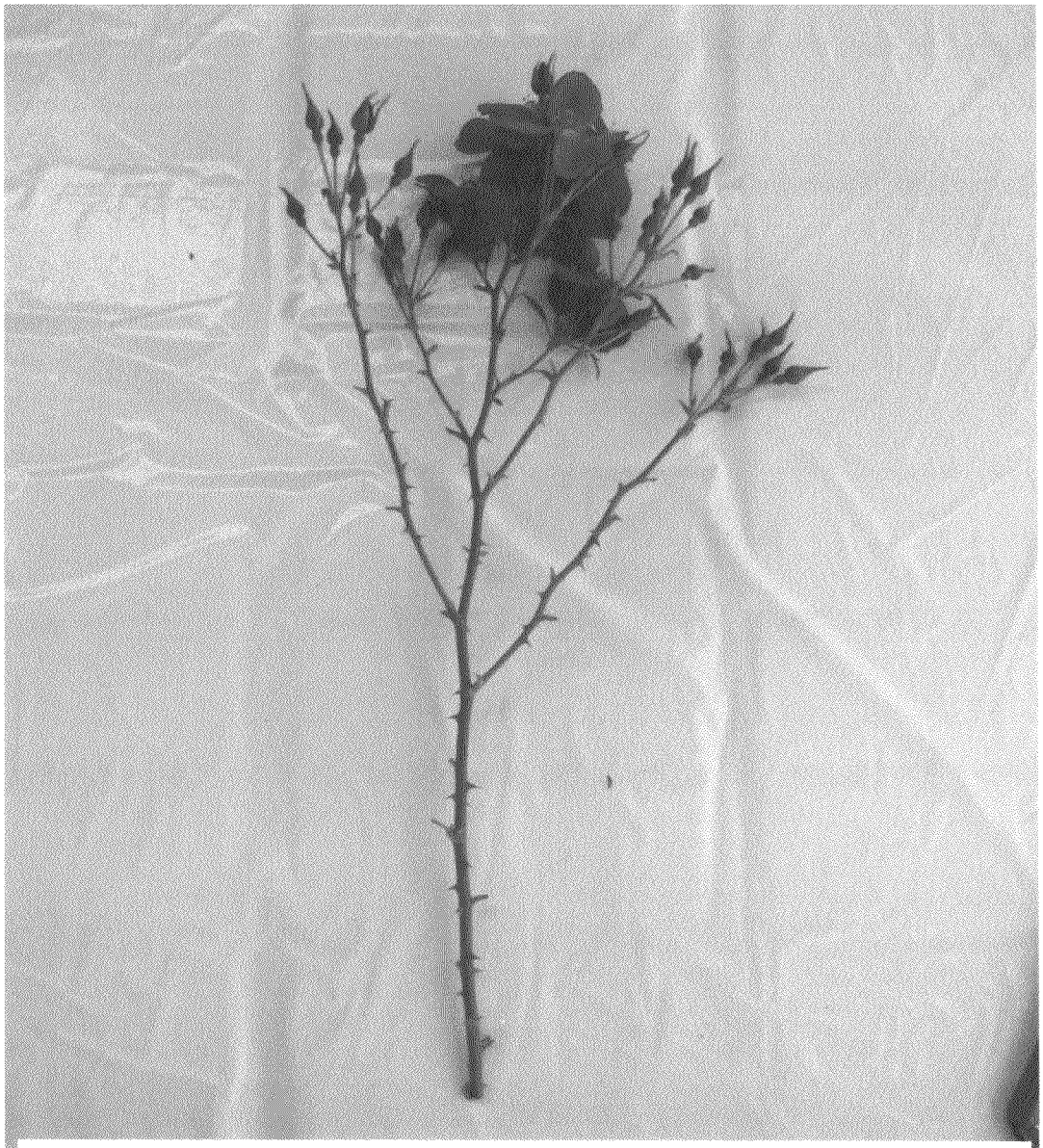
Figure 3:
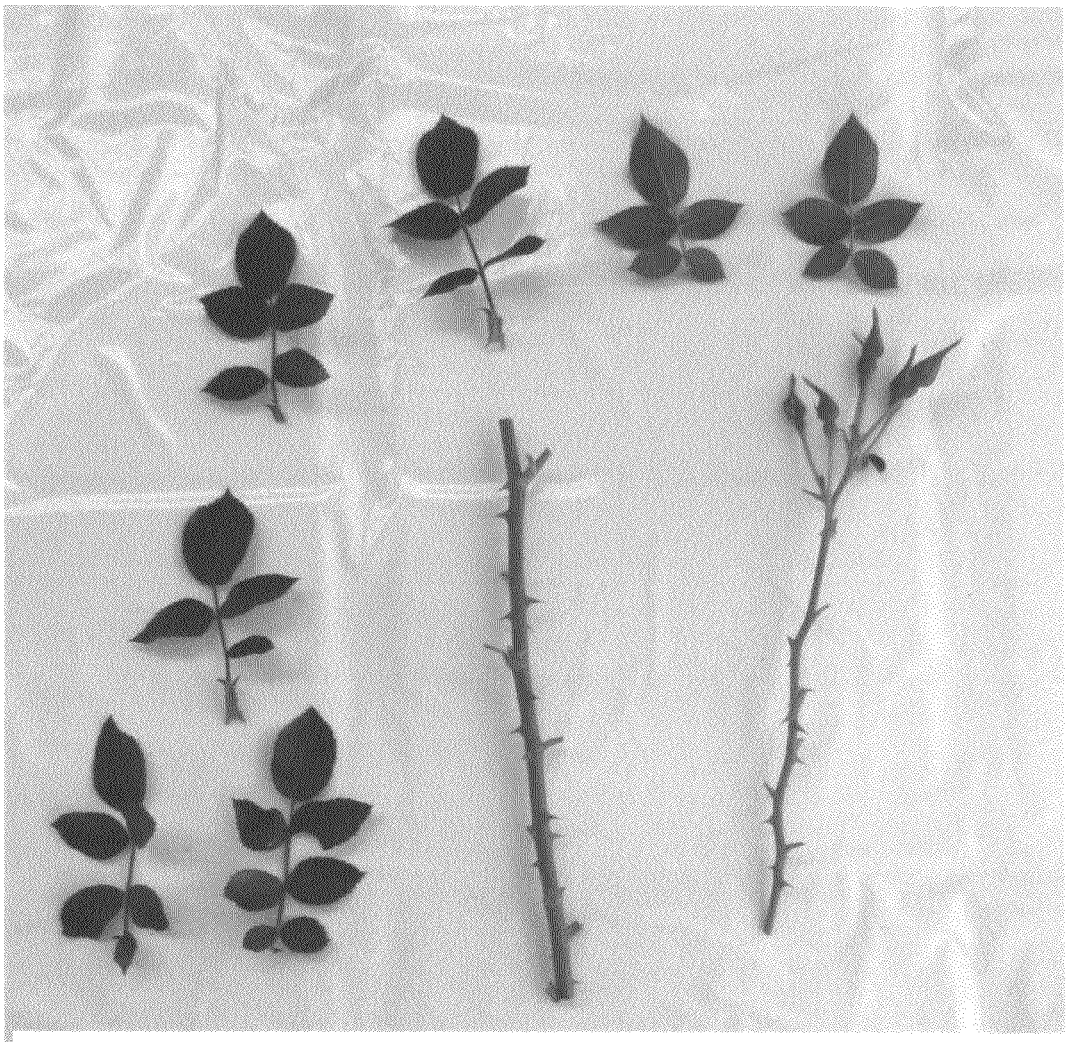

The following is a description of 'Poulcot012', as observed in its growth in in a field nursery in Marion County, Oreg. Observed plants are 3 years of age, and were grown on their own roots. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulcot007', U.S. Plant Pat. No. 16,985 are compared to 'Poulcot012' in Chart 1.

CHART 1

| | 'Poulcot012' | 'Poulcot007' |
|---|---|---|
| Petal Count | 5 | 20 |
| Flower Diameter | 40 to 50 | 40 mm |
| General Tonality of Flower Color | Red-Purple Group 57A | Red Group 45B |

FLOWER AND FLOWER BUD

Blooming habit: Continuous.

Flower bud:

*Size*.—Upon opening, 24 mm in length from base of receptacle to end of bud. Bud diameter is 8 mm.

*Bud form*.—Lanceolate.

*Bud color*.—As sepals divide petals are Red Group 53A.

*Sepal inner surface*.—Color: Yellow-Green Group 147C. Surface: Smooth. Weak pubescence.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have no foliaceous appendages.

*Sepal size*.—15 mm long by 4 mm wide.

*Receptacle*.—Texture: Smooth. Size: 5 mm in height by 4 mm wide. Color: Yellow-Green Group 144A. Shape: Elliptical.

*Pedicel*.—Surface: Smooth, with a few stipitate glands. Length: 20 to 30 mm. Diameter: 1 mm on average. Color: Yellow-Green Group 144D. Strength: Moderate.

*Peduncle*.—Length: 4 to 23 cm. Diameter: 2 to 4 mm. Color: Yellow-Green Group 144A. Surface: Small prickles.

Flower bud development: Flower buds are borne in clusters of 30 to 75 flower buds per stem, resembling a panicle.

Flower bloom:

*Fragrance*.—Light floral scent.

*Duration*.—The blooms have a duration on the plant of approximately 7 days. Petals fall cleanly away from plant after flowers have fully matured.

*Size*.—Flower diameter is about 40-50 mm when open. Flower depth is 10 mm.

*Flower shape*.—Single, fully open, and almost flat.

*Shape of flower, side view*.—The upper surface is flat. The lower surface is concave in shape.

Petalage: Under normal conditions, flowers have 5 petals total. No petaloids.

General tonality of flower: Open flowers Red-Purple Group 57A. Flowers become Red-Purple Group 57C before petal drop.

Petal color: Upon opening and after opening, petals are Red-Purple Group 57A on upper and lower surfaces. There is a Yellow Group 11D petal spot on the upper and lower surface.

Petals:

*Reflex*.—Weak.

*Margin*.—Entire and uniform. Weak undulations of margin observed.

*Shape*.—Generally narrow and elliptic. Apex shape: Emarginate. Base shape: Acute.

*Size*.—24 mm (l)×17 mm (w) on average.

*Texture*.—Smooth.

*Thickness*.—Thin.

Petaloids: None.

Reproductive organs:

*Pollen*.—Abundant, Yellow Group 11A.

*Anthers*.—Size: Approximately 1 mm in length. Color: Brown 200D. Quantity: About 90.

*Filaments*.—Color: Red-Purple Group 58C. Length: 6 mm.

*Pistils*.—Length: 3 mm. Quantity: 15 on average.

*Stigmas*.—Color: Yellow-Orange Group 20D.

*Styles*.—Color: Red Group 46A.

*Location of stigmas*.—Level in location relative to the length of the filaments and the height of the anthers.

*Hips*.—None Observed.

PLANT

Plant growth: Upright to bushy. Plants are 40 cm in height, and 40 cm wide.

Stems:

*Color*.—Juvenile growth: Yellow-Green Group 144A. Mature growth: Yellow-Green Group 144A.

*Length*.—On average, canes are 30 cm from the base of the plant to the flowering portion.

*Diameter*.—5 mm.

*Internodes*.—On mature canes, there is an average distance of 25 mm between nodes.

*Surface texture*.—Young wood: Smooth with few small prickles. Older wood: Smooth with few small prickles.

Long prickles:

*Incidence*.—13 prickles per 10 cm of stem.

*Size*.—Average length of prickles on mature stems is 8 mm.

*Shape*.—Upper and lower is concave.

*Color*.—Juvenile prickles: Greyed-Red Group 182B. Mature prickles: Greyed-Red Group 182C.

Plant foliage:

*Compound leaf*.—80 mm (l)×45 (w).

*Quantity*.—4 leaves per 10 cm of stem on average.

*Leaf bearing angle to the stem*.—45 degrees.

*Color of juvenile foliage*.—Upper side: Yellow-Green Group 144A. Lower side: Yellow-Green Group 144D. Anthocyanin: Greyed-Red Group 178A, shaded.

*Color of mature foliage*.—Upper side: Yellow-Green Group 147A. Lower side: Yellow-Green Group 147D.

Plant leaves and leaflets:

*Stipules*.—Size: 12 mm in length. Quantity: 2 per compound leaf. Shape: Linear, slightly broad based with outward extending apecies. Margins: Finely serrated. Color: Yellow-Green Group 146A.

*Petiole*.—Length: 10 to 16 mm. Diameter: 1 mm.

*Upper surface*.—Yellow-Green Group 146A.

*Lower surface*.—Yellow-Green Group 146, with small prickles.

*Rachis*.—Length: 16 mm on average.

*Upper surface*.—Yellow-Green Group 146A.

*Lower surface*.—Yellow-Green Group 146, with small prickles.

*Leaflet*.—Quantity: Normal number of leaflets leaves in middle of the stem is 5 to 7 leaflets. Margins: Serrated. Size: Average size of the terminal leaflet on normal leaves is 25 to 34 mm in length by 17 to 20 mm wide. Shape: Generally elliptical. Base: Rounded. Apex: Cuspidate. Texture: Smooth. Thickness: Average.

Arrangement: Odd pinnate. Venation: Reticulate. Glossiness: Moderately glossy.

Disease resistance: Above average resistance to powdery mildew *Sphaerotheca pannosa,* downy mildew *Peronospora sparsa,* rust, *Phragmidium* sps., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Shrub rose class named 'Poulcot012', substantially as illustrated and described herein, due to its abundant red flowers, disease resistance, and extended period of bloom.

* * * * *